United States Patent [19]
Coppersmith et al.

[11] Patent Number: 5,796,827
[45] Date of Patent: Aug. 18, 1998

[54] SYSTEM AND METHOD FOR NEAR-FIELD HUMAN-BODY COUPLING FOR ENCRYPTED COMMUNICATION WITH IDENTIFICATION CARDS

[75] Inventors: Don Coppersmith, Ossining, N.Y.; Prabhakar Raghavan, Saratoga; Thomas G. Zimmerman, Cupertino, both of Calif.

[73] Assignee: International Business Machines Corporation, Armonk, N.Y.

[21] Appl. No.: 749,865

[22] Filed: Nov. 14, 1996

[51] Int. Cl.$^6$ .................................................. H04L 9/00
[52] U.S. Cl. ................................. 380/9; 380/23; 380/52
[58] Field of Search ........................ 380/9, 4, 23, 52

[56] References Cited

U.S. PATENT DOCUMENTS

| | | | |
|---|---|---|---|
| 4,998,279 | 3/1991 | Weiss | 380/23 |
| 5,097,505 | 3/1992 | Weiss | 380/23 |
| 5,131,038 | 7/1992 | Puhl et al. | 380/23 |
| 5,168,520 | 12/1992 | Weiss | 380/23 |
| 5,361,062 | 11/1994 | Weiss | 340/825 |
| 5,367,572 | 11/1994 | Weiss | 380/23 |
| 5,724,423 | 3/1998 | Khello | 380/23 |

OTHER PUBLICATIONS

ICs For SmartCards, Leading-edge products with worldwide support. Philips Semiconductors.

Article, San Jose Mercury News, Business Monday, Monday, Oct. 21, 1996. By Janet Rae-Dupree, Mercury News Staff Writer, Can Touch This. Article on Tom Zimmerman, IBM Almaden Research, San Jose, Ca.

*Primary Examiner*—David C. Cain
*Attorney, Agent, or Firm*—Khanh Q. Tran

[57] ABSTRACT

An apparatus and method are disclosed for encoding and transferring data from a transmitter to a receiver, using the human body as a transmission medium. The transmitter includes an electric field generator, a data encoder which operates by modulating the electric field, and electrodes to couple the electric field through the human body. The receiver includes electrodes, in physical contact with, or close proximity to, a part of the human body, for detecting an electric field carried through the body, and a demodulator for extracting the data from the modulated electric field. An authenticator, connected to the receiver, processes the encoded data and validates the authenticity of the transmission. The apparatus and method are used to identify and authorize a possessor of the transmitter. The possessor then has secure access to, and can obtain delivery of, goods and services such as the distribution of money, phone privileges, building access, and commodities. Encryption provides rapid transmission and authentication of the transmitter, and a plurality of similar transmitters, with minimum vulnerability to counterfeit. Signal processing and digital communication components accommodate variations in location and orientation of the transmitter and receiver, and provide transmitters with long life times and high reliability.

17 Claims, 15 Drawing Sheets

; Synchronizer Pseudo-C Code
_____

; Given T,PUBLIC_ID,CARD_SEQUENCE from the Card
; Determine if CARD_SEQUENCE is valid.

; CARD_SEQUENCE is the bit sequence transmitted from the Card to the Authenticator, representing
; the content of one of the two registers (Register B or Register C) in the card. The register is selected
; in the Card based on the LSB of Register A.
;
; The length, number, and location of taps of the Card registers (Register A, B, and C) are known
; to the authenticator, by table lookup, using the public identification (PUBLIC_ID) as an index. The
; authenticator does not know the content of registers A, B, and C.
;
; The SYNCHRONIZER uses three independent Feedback Shift Register (FSR), labeled FSR_A, FSR_B,
; FSR_C, with the length, number, and location of taps specified by table lookup, indexed by PUBLIC_ID.
; Feedback shift register (FSR) reference page 655-657 The Art of Electronics, Horowitz and Hill,
; Cambridge University Press, Second Edition 1989.

FIG. 14A

; The SYNCHRONIZER creates the content of the card register (Register B or C) and authenticates by
; comparing the content of the created register (FSR_B or FSR_C) to the received sequence
; CARD_SEQUENCE.

```
K=T/2-2(square root(T));            // define constant
A_COUNT=0;                          // number of times FSR_A LSB is one
AUTHENTICATION_VALID=0              // reset authentication results for (=0;i<T;i++)                    // bring FSR_A up to time T
{       Clock FSR_A;
        if (FSR_A & 1)              // count number of times LSB of FSR_A is one
                A_COUNT++;
}
for (=0;i=K;i++)                    // bring FSR_B and FSR_C up to time K
{       Clock FSR_B;
        Clock FSR_C;
}
if (FSR_A & 1)                      // LSB of FSR_A selects FSR
{       for (i=0;i<A_COUNT-K;i++)   // bring FSR_C up to time T
                Clock FSR_C;
        if (FSR_C=CARD_SEQUENCE)    // check for authentication
                AUTHENTICATION_VALID=1   // match so valid
}
else
{       for (i=0;i<T-A_COUNT-K;i+)  // bring FSR_B up to time T
                Clock FSR_B;
        if (FSR_B=CARD_SEQUENCE)    // check for authentication
                AUTHENTICATION_VALID=1   // match so valid
}
```

SYSTEM AND METHOD FOR NEAR-FIELD HUMAN-BODY COUPLING FOR ENCRYPTED COMMUNICATION WITH IDENTIFICATION CARDS

FIELD OF THE INVENTION

The invention generally relates to the field of electronic communication systems. More specifically, the invention relates to the use of personal, electromagnetically encoded identification media for accessing information and services. The invention has particular applicability to credit cards, ID badges, etc.

BACKGROUND OF THE INVENTION

The use of electromagnetic fields as a communication medium is ubiquitous in today's society. Both communication over physical media, such as wires, and wireless communication, such as broadcast radio and television, are widespread and commonplace. Such communication may be made over long distances, including radio communication with space probes millions of kilometers away from Earth, or over much shorter distances, such as closed-circuit television or a client human being using a terminal to communicate with a local server.

In some situations, a user is physically present at a terminal or communication system, for the duration of a transaction. The terminal is available to all interested users, and a user having need of the service provided by the terminal seeks it out and uses it to make the transaction. Examples of such terminals are public pay telephones and Automatic Teller Machines (ATM).

Many transactions involve the use of a portable instrumentality for verifying the identity of the user, for authorizing the transaction, making a charge for the service, etc. Often, this instrumantality takes the form of a card bearing a magnetically encoded stripe, which is readable by the terminal. For instance, a user seeking cash from an ATM stands before the ATM, inserts his/her card, and keys in a Personal Identification Number (PIN), followed by menu-prompted transaction instructions. Authorization of the transaction is based on a verification of the user's identity based on a combination of (i) the user's possession of the authorizing card, and (ii) the user's knowledge of the PIN.

Since ATMs are generally located outside, there are numerous drawbacks for the user. For one thing, the user must key in his/her PIN at the beginning of the transaction. Even in relatively secluded ATMs, there is a significant likelihood that an interloper might observe the PIN as it is keyed in. The same drawback is also true for other forms of public transactions, such as a calling card call at a public telephone booth.

Also, the user, while conducting the transaction, is vulnerable to being assaulted, or to having his/her card or cash grabbed and stolen. Moreover, many ATMs operate by ejecting the card part way out of the slot after a first transaction. The user can either take the card, indicating that he/she requires no further transaction, or leave the card there and continue keying in instructions for another transaction. During the second transaction, the card is right there in the open, accessible to anyone who might want to reach in, grab it, and run. Therefore, the accessibility of the ATM card, while the user is handling it or using it, presents the drawback that there is a significant vulnerability to loss or theft.

Therefore, there is a need for a form of communication which reduces the user's vulnerability to theft or attack by making such instrumentalities less accessible to persons other then the owner.

A new approach, recently emerging, for implementing electronic communication takes advantage of the fact that the human body is made up largely of electrolytic fluids, and is therefore capable of carrying electrical signals itself.

In a co-pending United States Patent Application by David Allport, Neil Gershenfeld, and Thomas Zimmerman, "Non-Contact System for Sensing and Signaling by Externally Induced Intra-Body Currents" (Ser. No. not available), there is described a wireless system in which a transmitter and a receiver are coupled, by touch or by close proximity, through a user's human body. (The electrical circuit is completed by close proximity with the floor, which is treated as an electrical ground.)

The transmitter produces low-frequency, low power signals that, through capacitive coupling, pass as displacement currents into and from the body of the user. The user's body acts as a conductive medium. A receiver that is capacitively coupled to the user's body responds to the displacement currents passed to it from the user's body, to detect the low frequency signals.

The signal transmitted by the transmitter is preferably a carrier, modulated with the information to be transmitted using a pseudorandom code, to produce spread spectrum signals. Such modulation provides noise immunity, and allows multiple transmitters, each using a different modulation code, to operate simultaneously.

Electrodes, preferably small and flat, are used for coupling electronic devices to the human body. The electrodes may be incorporated into items that are routinely in contact with the human body, such as wristwatches, clothing, or shoes. The electrodes can also be incorporated into items not directly in contact with the human body, but which are within the close vicinity, such as a credit card carried in a wallet.

Certain further aspects of such a system are described in the newspaper article, "Can Touch This," San Jose Mercury News, Oct. 21, 1996, and in Zimmerman, "Personal Area Networks: Near-Field Intrabody Communication," IBM Systems Journal, Vol. 35, Nos. 3, 4, 1996, which are incorporated by reference herein. In the former article, the interviewee is quoted as saying that an issue remaining to be dealt with is that of privacy, in which the user seeks to control and limit the information which is transmitted by such an apparatus.

Thus, these prior art systems do not teach how to avoid unintended interception and reproduction by a foe. The question of how inter-body EF communication can be used in intrusion-sensitive applications, particularly in monetary exchanges or identity verification, is not addressed by any of the above-discussed references, and remains to be solved.

SUMMARY OF THE INVENTION

It is therefore an object of the invention to provide an apparatus and method for utilizing the human body as a communication medium for transmitting information related to the user, which allows the user to protect privacy.

It is a further object of the invention to provide an apparatus and method for utilizing the human body as a communication medium for transmitting information related to the user, which protects the confidentiality of the information against parties not authorized or desired by the user to have access to the information.

It is a further object of the invention to provide an apparatus and method for utilizing the human body as a communication medium for transmitting information related to the user, which does not allow unauthorized parties to produce messages which are apparently originated by the user.

To achieve these and other objectives, there is provided in accordance with the invention a communication system which produces small currents in the human body, externally induced by electrostatic field coupling, and which provides for wireless identification and authentication among proximate devices.

The present invention provides an apparatus and method for encrypting data for transmission through the human body, which uses a modulated electric field, which provides for easy and rapid receipt and authentication, and which has sufficient capacity to handle millions of unique transmitter codes.

It is an object of the invention to be practical for deployment among a population of millions, at an acceptable cost, and at a high degree of security and performance. To these ends, the invention addresses the following issues: encryption, dynamic range, low power operation, multiple functions, multiple transmitters, and efficient decryption.

The encryption preferably is computationally simple enough to be performed on a low cost microcomputer. Such a microcomputer, in a preferred implementation, operates on the order of 0.1 to 1 million instructions per second. The preferred implementation of the invention uses encoding means that can produce a code sufficient to identify ten times the population of the earth in less than 8,000 instructions.

Provisions are made for the possibility of a transmitter being lost or stolen. Decryption preferably should be possible in a reasonable time, typically under one second. It is an object of the present invention to provide a decryption scheme that can handle thousands of users with a response time on the order of seconds or less.

The signal strength detected at the receiver can vary dramatically since it is dependent on the location and orientation of the transmitter and receiver, the former of which is usually on a person's body and therefore cannot be constrained. A reliable robust authentication system must assume large changes in received signal, typically in excess of 60 dB. It is an object of the present invention to provide a system capable of handling the dynamic range typically encountered.

For maximum convenience, the device on the person's body should not require interaction by the person. Authentication should happen automatically, without intervention by the person. For instance, where the instrumentality is a card carried in the user's wallet, it should not be necessary for the user to get the card out, or take any other physical action to cause the card to undergo the required communication.

The device should also operate for a reasonably convenient lifetime, preferably at least one or more years, requiring little or no maintenance, repair or replacement. If the device is battery-powered, it should therefore consume little enough power to allow for a suitably long battery life. It is an object of the present invention to provide such a low-power, zero-maintenance device.

It is not unusual for a person to carry six to ten cards in his/her wallet. Thus, several cards in accordance with the invention may be carried, each of which containing digital information in the form of text or a magnetic strip. Since the invention requires electronic circuitry, and will be more expensive than a piece of plastic, it is desirable to minimize the number of such devices carried in a wallet. Ideally one device could replace the function of all the cards in a person's wallet. Alternatively, if several such devices are carried in a wallet, they should work in a way that does not hamper their mutual operation. It is an object of the present invention to provide one card to replace the function of many. It is a further object of the present invention to provide a system wherein several transmitters can be carried by a person without hampering their mutual operation.

While the invention is primarily disclosed as an apparatus, it will be understood by a person of ordinary skill in the art that a system, such as a conventional data processor, including a CPU, memory, I/O, program storage, a connecting bus, and other appropriate components, could be programmed or otherwise designed to facilitate the practice of the invention as a method. Such a processor would include appropriate program means for executing the method of the invention.

Also, an article of manufacture, such as a pre-recorded disk or other similar computer program product, for use with a data processing system, could include a storage medium and program means recorded thereon for directing the data processing system to facilitate the practice of the method of the invention. It will be understood that such apparatus and articles of manufacture also fall within the spirit and scope of the invention.

BRIEF DESCRIPTION OF THE DRAWINGS

FIG. 14 is a pseudocode embodiment of a component of the invention.

DESCRIPTION OF THE PREFERRED EMBODIMENT

Figure 1:
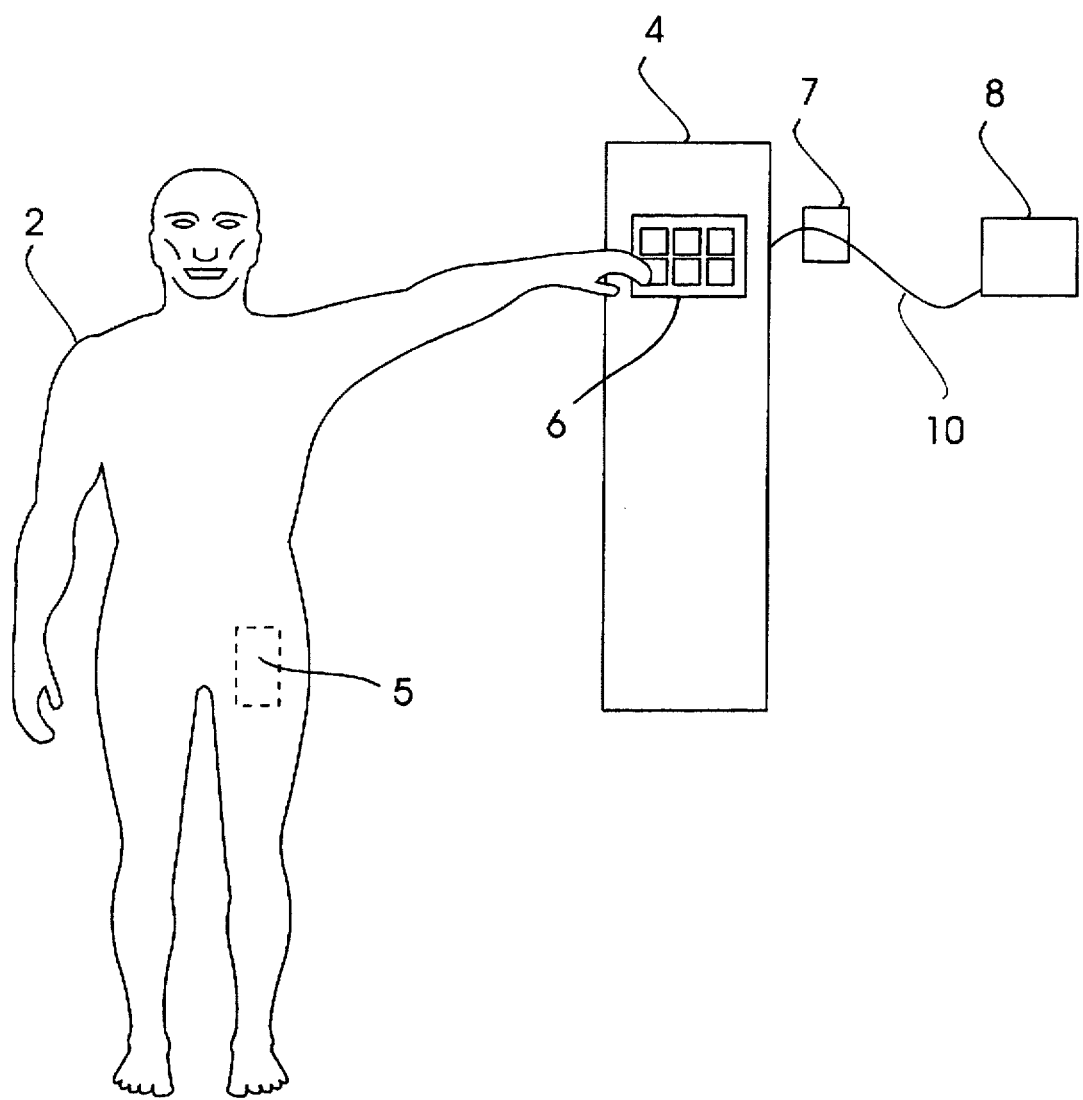
FIG. 1 is a drawing of a typical application of a personal area network including a remote authenticator, according to the invention, where a person is activating an automated teller machine (ATM).

General Discussion of Use of Human Body as Communication Medium

It is a particular advantage of the invention that communication through the human body is less accessible to eavesdropping than wireless communication is. The following comments, relating to parallel areas of development in the wireless communication technologies, illustrate drawback which are overcome by human-body communication according to the invention.

Current work on wireless networks is focused on infrared (IR) light technology and radio transmission. Light-based communication systems require a direct line of sight from the transmitter to the receiver. Light-based communication also requires an optical aperture. This precludes putting a device using such technology into a user's pocket, or otherwise concealing it on the user's person.

Typically infrared (IR) emitters are used in wireless networks which consume up to 1 watt, an excessive amount of power for a battery powered device such as a watch or pager. A common standard for battery powered watches is that the batteries should last for three years. Therefore a preferred communication system would consume little enough power to have a comparable lifetime.

Radiofrequency (RF) badges are also used. Such badges commonly take the form of a card having an RF transmitter, as described in co-assigned U.S. Pat. No. 5,5238,222, issued Jun. 18, 1996.

Radio transmissions introduce a host of problems. Radios use antennas to converts electric waves into propagating electromagnetic waves. Antennas need to be on the order of one half a wavelength long for efficient transmission and reception. Considering that the body located devices are typically less than 100 mm long, a carrier in excess of 1 GHz is necessary, a frequency up in the microwave region. Such high frequencies require circuits that consume significant power.

Antennas require a particular geometry, either long and thin to capture the electric field, or coiled to capture the magnetic field of electromagnetic radiation. A preferred communication system could conform to, and take advantage of, the geometry of the object it is embedded in.

Radio frequencies in the GHz range begin to share the directional properties of light. The body appears as an electrical conductor due to the presence of ionic electrolytes in the blood. This poses a difficult problem for two devices attempting to communicate which are located on opposite sides of the body, for example an electronic watch on the right hand and a battery powered microchip calling card in the left back pocket. A preferred communication system would be able to communicate among devices located anywhere on the body.

Another consideration is that radio transmissions are subject to the field strength and frequency limitations of the FCC. These regulations can introduce lengthy delays in releasing a product. A preferred communication system would not be subject to licensing by the FCC.

Antennas have preferred directions, transmitting energy in beam patterns rather than omnidirectionally. However the designer of an electronic device to be located on the body may not always know where the device may be located. The device may have to communicate on a range of locations and orientations in the course of normal ware. For example, a wristwatch moves and changes orientation along with the user's hand movements. A preferred communication system would have great flexibility in orientation, operating over a range of motion and location.

A radiated signal can be intercepted at any distance with a large enough antenna. This is the nature of broadcasting. Some of the data transferred among personal electronic devices will probably be of a sensitive nature, for example credit card and telephone numbers, client notes, personal diary entries, business communications, and computer identification passwords. The best security is a communication system where messages cannot be intercepted. What is needed is a communication method that makes it difficult to intercept messages.

It is not uncommon to have many people together in a small space, such as in public transportation, elevators, queuing lines, conferences, and audiences. Under these circumstances it would be unacceptable to have a communication system fail due to interference from neighboring communication system. Since the communication of these personal electronic devices occurs over a limited distance (for example under two meters) it would be beneficial for the communication system to have limited range.

Therefore, the objectives of a desirable personal area network communication system may be summarized as follows:

1) Currently there is no standard method to interconnect these personal electronic devices. Electrostatic coupling (ESC) can be used for a range of devices.

2) A need exists for some type of wireless, but preferably not over-the-air (RF), networking, similar to the type used by computers, such as wireless local area networks (LANs), for these sensors, and other electronic devices, to share data. ESC can provide the physical interface to a network structure.

3) A preferred communication system should consume little power. Because ESC operates at lower frequencies than radio, no energy is radiated, and low power is consumed.

4) A preferred communication system would have great flexibility in orientation, operating over a range of motion and location. A preferred communication system would be able to communicate among devices located anywhere on the body. ESC uses the body as part of the communication circuit, and uses every material in the environment for the return current path.

5) A preferred communication system would not be subject to licensing by the FCC. The electric field strengths used in the preferred embodiments of the invention are orders of magnitude lower than those set by the FCC. For example, a typical ESC device measuring 80 mm×50 mm×8 mm (a thick credit card), transmitting at 330 kHz at 30 volts (typical for a resonant transmitter) has a field strength of 344 pV/m at 300 meters, 86 dB below the FCC allowable field strength as specified in the FCC Part 15 regulations.

6) What is needed is a communication method that makes it difficult to intercept messages. Since electric field falls off as distance cubed, at ten times the distance the field is 1/1000 the intensity. As the distance from the transmitter increases, the signal strength rapidly falls below the thermal noise of the environment, making eavesdropping increasingly difficult to impossible.

7) Non-interference from neighboring systems. Electrostatic communication systems have limited range. Again, electric field intensity falls off with distance cubed, so neighboring devices only hear their neighbors. Signals from devices further away quickly fade away to inaudibility.

8) Antenna size is small and flat, or can take the shape of the object it is embedded in. The electrode effectiveness depends on the projected surface area. It does not rely on a particular exacting shape and geometry. Wristwatch bands meet this requirement. Credit cards are particularly good, because they present a relatively large surface area. Shoe soles also have large surface areas, and make unusually good contact with both the ground (outer electrode) and the user's body (inner electrode), making them great candidates for communicating with other devices positioned around the user's body.

Cryptography

The present invention provides a method to encrypt data for transmission through the human body using modulated electric field so that it can be received and rapidly authenticated, with sufficient capacity to handle millions of unique transmitter codes. To be practical for deployment among a population of millions, at an acceptable cost and high degree of security and performance, the present invention address the following issues; encryption/decryption, dynamic range, low power operation, multiple functions, multiple transmitters, and efficient decryption.

The encryption must be computationally simple enough to be performed on a low cost microcomputer, which operates on the order of 0.1 to 1 million instructions per second. The preferred algorithms for encryption do not employ multiplication, modular exponentiation, or other operations that are difficult to perform in inexpensive processors. The present invention uses encoding means that can produce a code sufficient to identify ten times the population of the earth in less than 8,000 instructions.

Provisions must be made for the possibility of a transmitter being lost or stolen. Decryption must be possible in a reasonable time, typically under one second. It is an object of the present invention to provide a decryption scheme that can simultaneously handle thousands of users with a response time on the order of seconds or less.

The signal strength detected at the receiver can vary dramatically since it is dependent on the location and orientation of the transmitter and receiver, the former of which is usually on a person's body and therefore cannot be constrained. A reliable robust authentication system must assume large changes in received signal, typically in excess of 60 dB. It is an object of the present invention to provide a system capable of handling the dynamic range typically encountered.

For maximum convenience the device on the person's body should not require interaction by the person. Authentication should happen automatically, without intervention by the person. The device should also operate for one or more years, minimizing maintenance and repair or replacement. If the device is battery powered, it should therefore be a low power device to maximize battery life. It is an object of the present invention to provide a low power zero maintenance device.

It is not unusual for a person to carry six to ten cards in his/her wallet. Each card contains digital information in the form of text or a magnetic strip. Since the invention requires electronic circuitry and will be more expensive than a piece of plastic, it is desirable to minimize the number of devices carried in a wallet. Ideally one device could replace the function of all the cards in a person's wallet. Or if several devices are carried in a wallet, they should work in a way that does not hamper their mutual operation. It is an object of the present invention to provide one card to replace the function of many. It is a further object of the present invention to provide a system wherein several transmitters can be carried by a person without hampering their mutual operation.

Discussion of Illustrated Embodiments

FIG. 1 is a drawing of a typical environment in which a personal area network including a remote authenticator, according to the invention, is used. It will be understood that numerous other environments may also employ the invention. Such other environments include public telephones which accept calling card calls, gas pumps at service stations, photocopy machines, postal meters, and entry through building or automobile doors. Also, the invention may be used in connection with computer keyboards as a password mechanism. When the user lifts his/her hands from the keyboard, the machine locks up.

Referring now to FIG. 1, a person, or user, 2 is activating an automated teller machine (ATM) 4. The person 2 is carrying a personal area network (PAN) instrumentality 5, such as an EF card (described in detail below). The ATM 4 includes a control panel 6, which includes suitable keys for allowing the user 2 to key in suitable information such as a PIN and the desired transaction. The control panel 6 includes a contact for establishing an electrical coupling with the person 2.

The ATM 4 is coupled to a receiver module 7 and a processor 8 by means of a communication link 10. Typically, the processor 8 is located at a remote site, and the link 10 includes a suitable medium such as the telephone network. The processor 8 has all required facilities for processing the user's 2 transaction request, such as access to a database of the user's 2 account, etc.

The PAN card 5 and the processor 8 communicate, through the conductive medium of the user's 2 body and the link 10, to verify the user's 2 identity.

In accordance with the invention, the communication is encrypted to establish authentication and security. The preferred technique of encryption is described in detail below.

Also, if the user carries multiple PAN-type transmitters, such as instrumentalities embedded in cards, a watch, or shoes, these may be separately detected for authentication.

In accordance with the invention as illustrated in FIG. 1, a transmitter and a receiver work in combination to provide the communication. For bidirectional communication, two transceivers are used. They are located, for instance, in the card 5 and the processor 8 of FIG. 1

Figure 2:
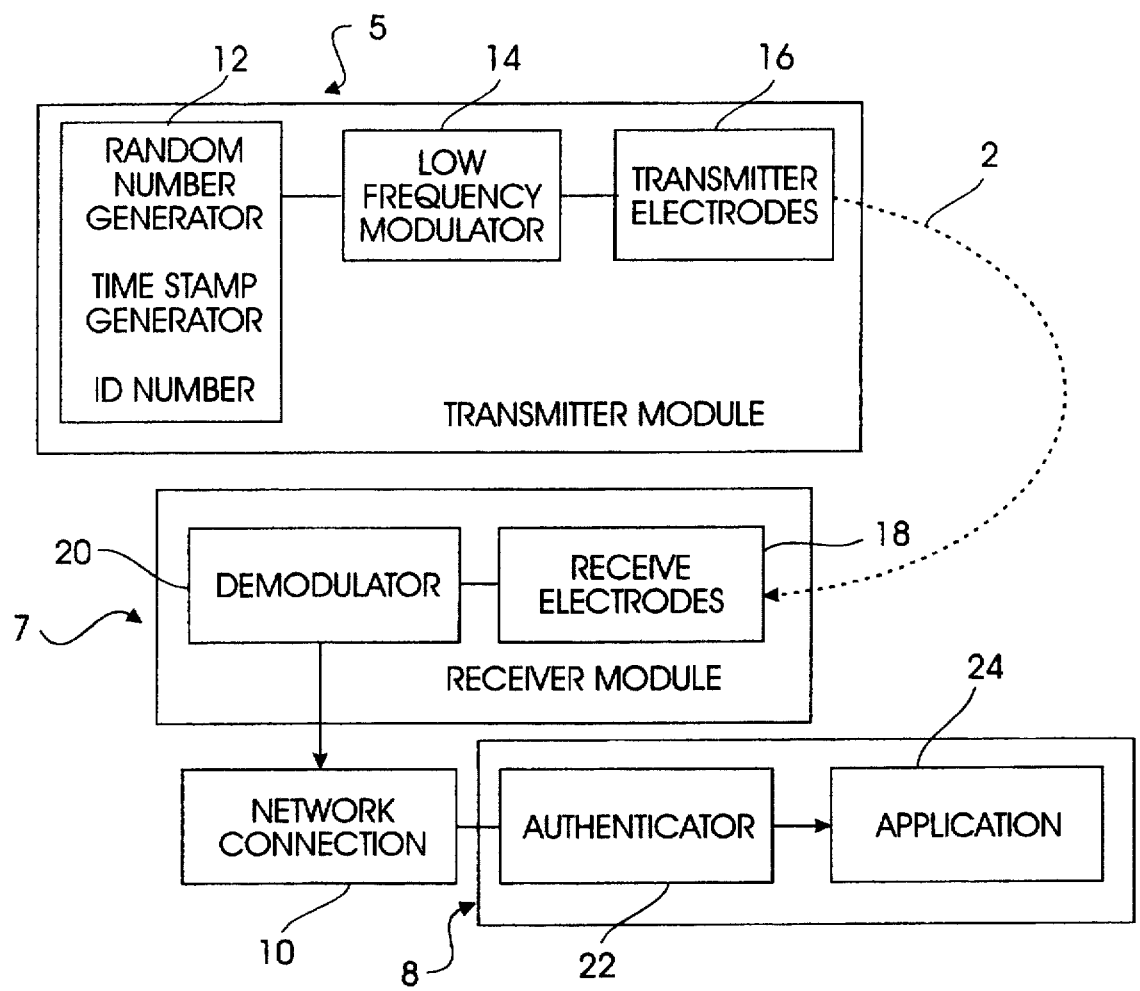
FIG. 2 is a functional block diagram of a transmitter and receiver module.
Figure 3:
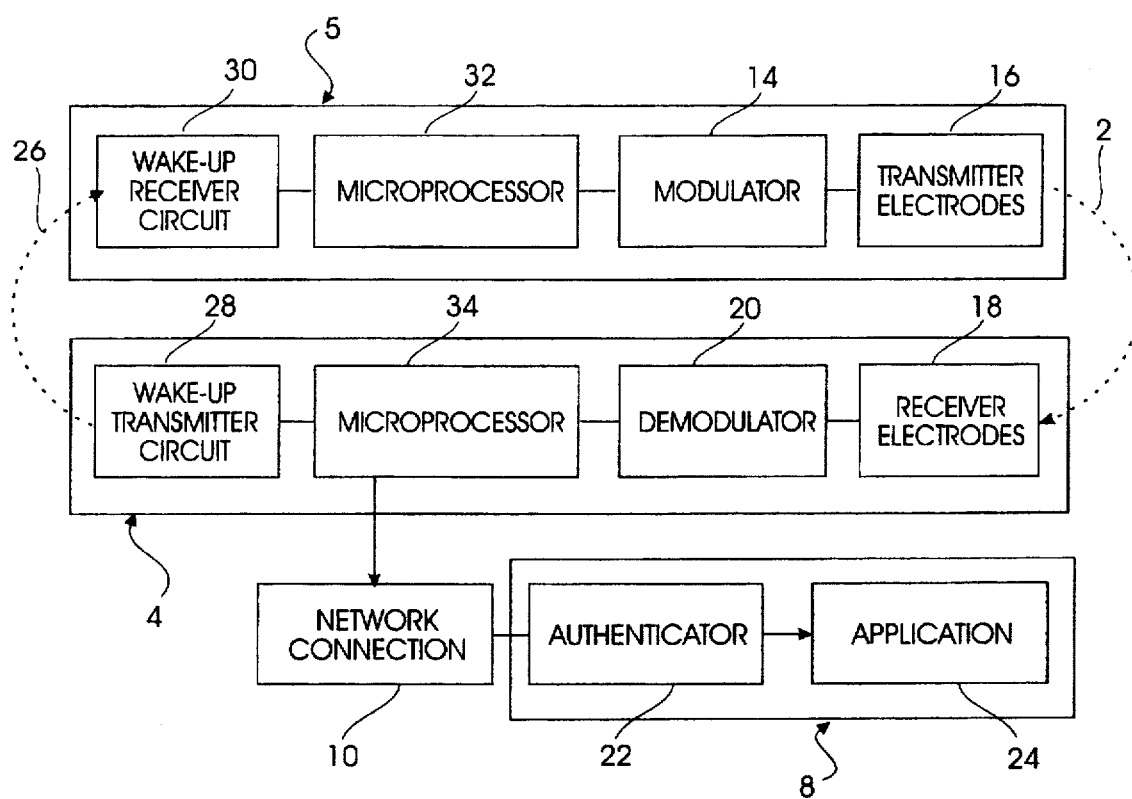
FIG. 3 is a functional block diagram of a transmitter and receiver module, where the receiver module wakes up the transmitter module.

FIGS. 2 and 3 are functional block diagrams of two preferred embodiments of these transmitter and receiver modules.

In FIG. 2, unidirectional communication takes place between a transmitter and a receiver. This system supports a scenario in which the card 5 continuously, or at regular intervals such as every second, transmits a signal such as an ID (see below). The assumption is that, whenever the user 2 touches a control panel 6, within a suitably short time, the regularly transmitted ID signal passes into the control panel for receipt by the processor 8. Thus, no prompting or handshaking is required.

In such an embodiment, the card 5 includes a transmitter module shown in detail. As will be discussed below, the transmitted signal is encrypted in accordance with the invention. Accordingly, the card 5 includes a signal generator 12 which produces an encrypted signal based preferably on a random number, a time representation, and a user ID. The resultant signal is modulated using a low frequency modulator 14, and transmitted to the user's 2 body tissues due to the proximity of the card 5 to the user's 2 body. The user's body 2 is represented schematically in FIG. 2 as a unidirectional communication line.

The receiver 4 is coupled to receive the signal because of the user's 2 physical contact with a receive electrode 18 on the control panel 6. The signal is demodulated by a demodulator 20, and passed through the network link 10 to the processor 8. Within the processor 8, an authenticator 22 authenticates the signal in accordance with the encryption protocol described in detail below, and provides the information to an application 24, such as a program for processing ATM transactions.

In FIG. 3, bidirectional communication takes place between a transceiver in the card 5 and one in the ATM 4.

This alternative system supports a scenario in which the card 5 saves power by transmitting a signal (such as an ID (see below)) only when requested to do so. The assumption is that, whenever the user 2 touches a control panel 6 and begins a transaction, the control panel 6 requests the signal, and the card 5 responds by sending the signal. Thus, a prompting or handshaking sequence is performed.

Some of the components in FIG. 3 are equivalent to the similarly numbered components of FIG. 2. However, a separate communication signal 26, the aforementioned request, travels through the user's 2 body from the control panel 6 to the card 5. That request is generated by a wake-up circuit 28 in the ATM 4, and is received by a wake-up receiver circuit 30 in the card 5. The wake-up circuit 30 preferably controls a power-save function on the card 5, to reduce power consumption during idle periods, and to restore full power upon receipt of a request.

When power is restored, a microprocessor circuit 32 generates an encrypted signal, in much the same manner as the generator 12 of FIG. 2. The ID signal is routed, as before, to the ATM 4, where a microprocessor 34 directs transmission of the demodulated signal through the network 10 to the processor 8, as before.

The microprocessors, particularly the microprocessor 32 on board the card 5, is preferably a low-frequency unit, such as a CMOS microprocessor, for low power consumption. Because of the large number of cards 5, relative to the number of ATMs 4, the cost of microprocessors, and of the circuitry in general, is preferably asymmetric. That is, abundant, cheap transmitters (one per person), but few expensive receivers (one per ATM machine, car, door, etc.) are used. Also, preferably the transmitter employs relatively simple circuitry, while the receiver may be more complex.

The system preferably employs a combination of encryption generated by the card 5, such as a perishable password random number generator (described in detail below), and a PIN keyed in by the user 2.

Preferred Embodiment of EF Card

Figure 4A:
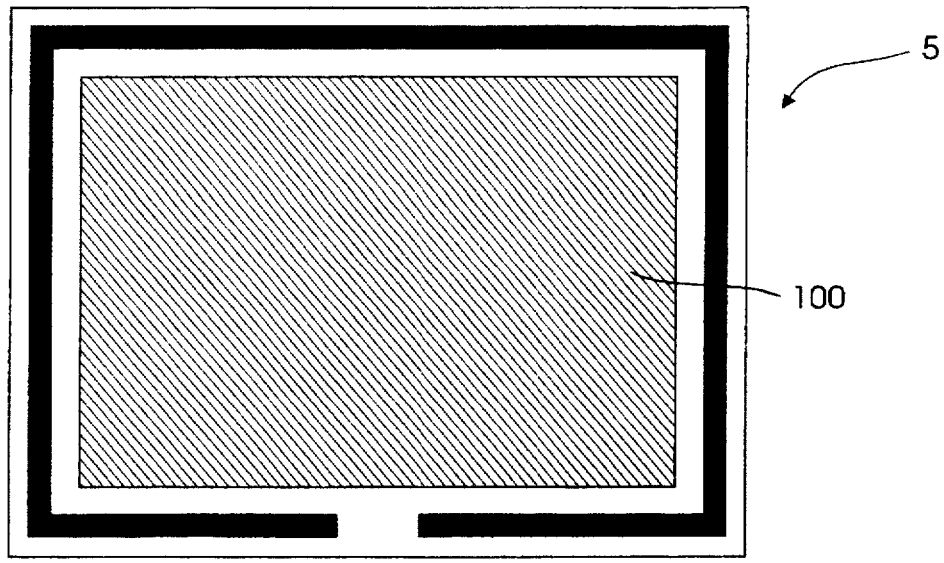
FIG. 4A, 4B, and 4C are top, bottom and side cross-sectional views of a typical transmitter designed to fit in the format of a thick credit card.
Figure 4B:
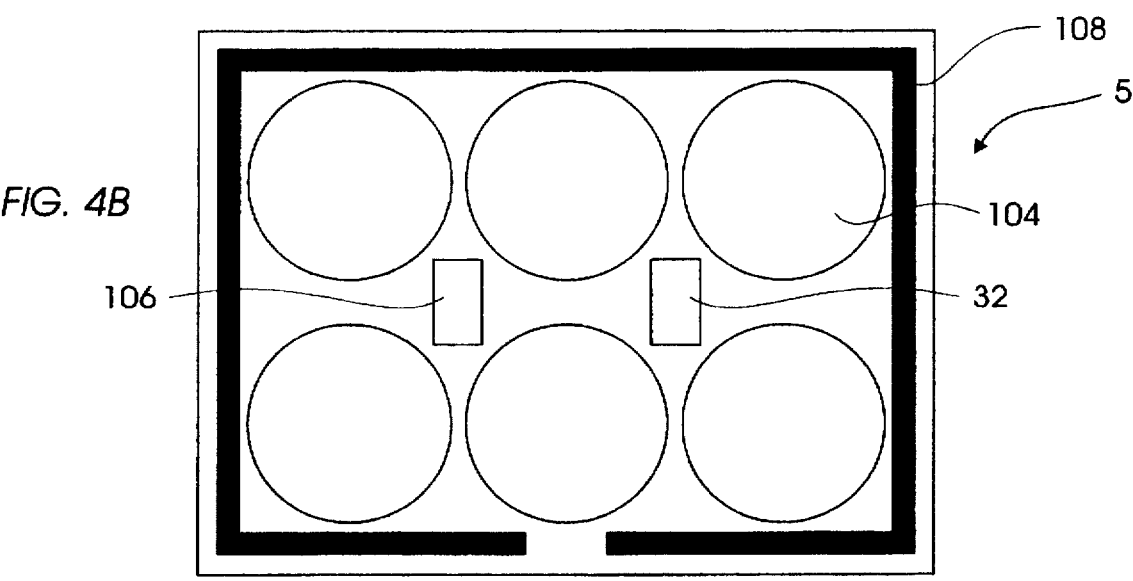
Figure 4C:
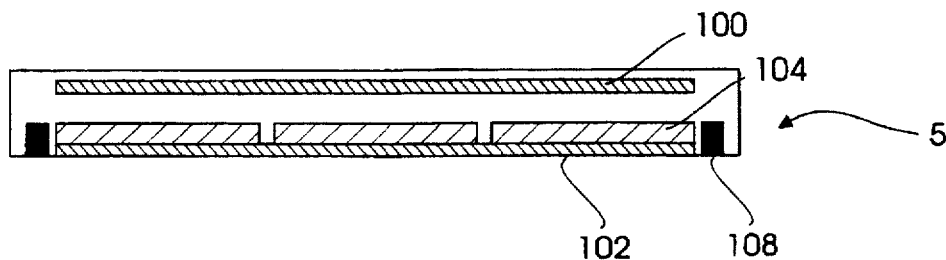

FIGS. 4A, 4B, and 4C are cutaway top, bottom, and side views, respectively, of a preferred embodiment of the card 5, designed to fit in the format of a thick credit card. The card 5 incorporates a transmitter 5 as per FIG. 3.

The transmitter 5 has a top electrode 100 and a bottom electrode 102. The transmitter is large enough to include six coin-sized lithium cell batteries 104, typically providing over 2 years of battery life. Electronics 106, including a microprocessor 32, are located in between the batteries 104 for efficient use of card area.

A loop antenna 108 detects a communication signal 26, which wakes up the microprocessor 32 to minimize power consumption in between data communication. The loop antenna 108 dimensions, and the communication signal 26, are chosen to optimize signal coupling efficiency between the card 5 and the ATM 4.

By making the perimeter of the loop substantially near ½ the wavelength of the communication signal 26, the radiation pattern of the loop 108 will have no null, minimizing the sensitivity of the card 5 to orientation. A preferred communication signal 26 frequency would be between 100 MHZ and 500 MHZ. The communication signal 26 can be as simple as a constant carrier which is always on.

When a card 5 gets sufficiently close, the voltage generated at the loop 108 will be sufficient to turn on the microprocessor 32. If several people are near the ATM 4, and their respective cards 5 are turned on, then only the person touching the ATM receiver electrode 18 will be detected.

An on/off switch may be provided to turn the unit off when communication is not desired. A preferred method is to slip a metal case around the card 5. This will block RF from reaching the device. Additional buttons can be placed on the card 5 (not shown) to allow several functions to be selected among, for instance, multiple credit cards owned and carried by one person. A preferred method is to have the ATM 4 display the cards (actually the accounts) available to the user 2, and have the user 2 select the desired account on the control panel 6.

Figure 5A:
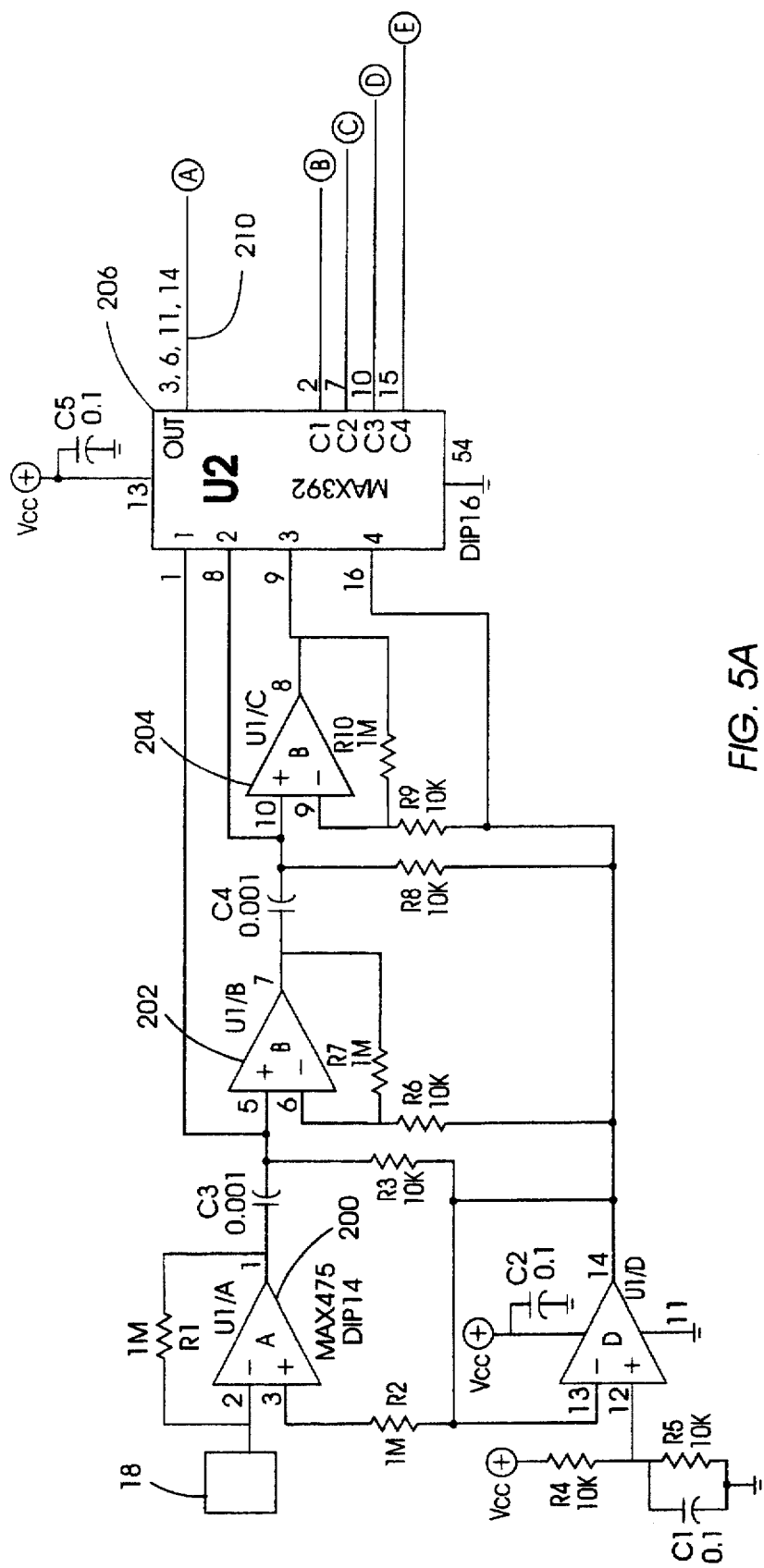
FIG. 5 shows an electronic schematic of a typical receiver circuit.
Figure 5B:
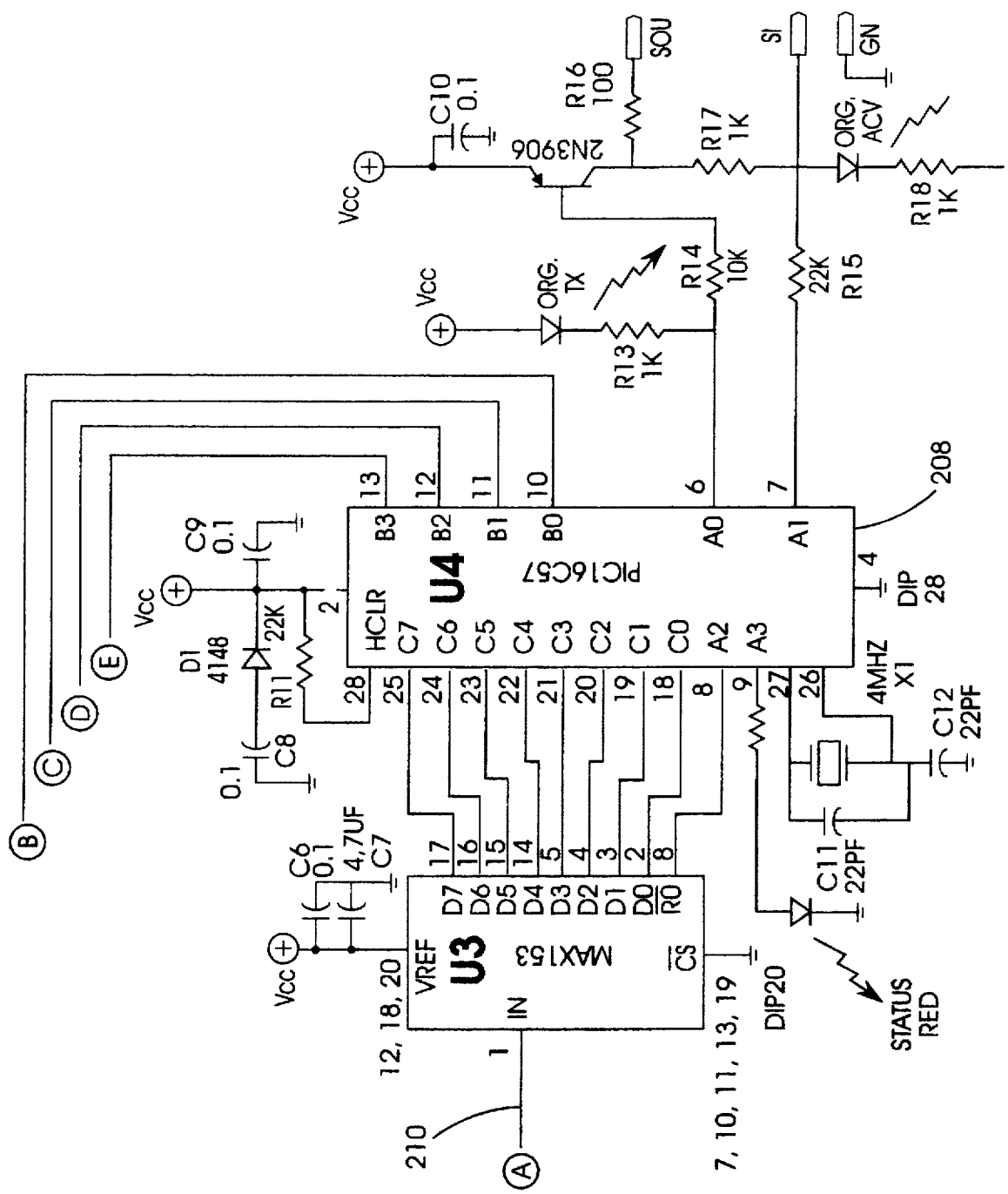

FIG. 5 shows an electronic schematic of a typical receiver circuit. The receiver detects a small displacement current on the receiver electrode 18. An amplifier 200 amplifies and converts the displacement current into a voltage. Amplifiers 202 and 204 provide further stages of amplification. A digitally controlled switch 206, controlled by a microprocessor 208 (such as PIC16C57 sold by Microchip Technology (Chandler, Ariz.)), selects one of the amplifier outputs and applies the amplified signal 210 to a fast analog-to-digital converter 212, such as a MAX153 sold by Maxim Corporation (Sunnyvale, Calif.), which is capable of 1 million conversions per second at 8 bits.

The result is a general purpose data acquisition of displacement current with a dynamic range in excess of 60 dB. Once the data samples are captured in the microprocessor 208, many types of communication demodulation techniques may be applied.

A preferred communication demodulation technique is direct sequence spread spectrum, as described by Leon W. Couch in Modern Communication Systems (Prentice Hall, N.J., 1994) page 380–387. A preferred method of using spread spectrum to allow selective detection of multiple transmitters is to have each transmitter synchronize to the phase of the communication signal 26, and to delay the pseudo-random sequence based on the individual unique ID number of each transmitter. To select among multiple transmitters, the receiver would slip the phase of the correlation function, looking for peaks in the autocorrelation function (see page 384 of Couch).

A alternate embodiment of communication demodulation technique is On-Off Keying, whereby a 1 is represented by the carrier on, and a zero by the carrier off. This scheme of amplitude modulation (AM) is less complex than spread spectrum, and multiple transmitters may be selected based on signal strength.

In a preferred embodiment, the EF Card produces an ever-changing encrypted output to prevent an eavesdropper from capturing an output and playing it back later. The microcontroller in the card contains the user's unique public ID number (64 bit), a unique private key (64 bit), a unique private time offset (64 bits) and a program to generate a DES encrypted output. Every second the EF Card transmits three pieces of information the EF Card's time-of-day, the user's public ID number, and an encrypted version of a random number generated by an offset version of the EF Card's time-of-day and the private key (64 bit result). The reader detects these three values, and sends them to a secure authentication machine, which confirms the validity of the code.

The authenticator contains a data base of every user's public, private, and time offset values. The authenticator uses the public id to look up the time offset and private key, and encrypts the offset time using the same DES algorithm to check the validity of the EF Card.

The microcontroller uses an inexpensive watch crystal to maintain a time base to within minutes per year. The time base is used to generate pseudo-random numbers with a feedback shift register (XORing multiple taps of a shift register). A private offset is added to the transmitted time-of-day, so an eavesdropper would not know what random number was generated even if they knew the random number table.

The only known weakness in the system is that the authenticator must allow for a variation in the EF Card's time keeper, due to the temperature dependence of the EF Card's time reference crystal, which is 50 ppm from −10 to 60 degrees C. This produces a vulnerability time window where an eavesdropper can record the output of an EF Card, and rebroadcast it within a temporal acceptance window. The error and acceptance window grows with time, and is reset every time the EF Card authenticates.

The theoretically worst case would be 26 minutes per year, but since the EF Card is typically carried by a user on his/her person, it is fair to assume that the user's body, and therefore the card, will be maintained nominally at room temperature. The validity of this assumption is demonstrated by the fact that a low-cost (under $10) electronic wrist watch varies less than a few minutes per year.

By setting limits on the size of the window, periodic authentication is required, and security vulnerability is limited.

In a preferred embodiment, the EF Card contains a microcontroller that operates at a low frequency (32 kHz), drawing 28 uA (microamps) at 2.5 volts. Transmission (oscillating the plates of the credit card) consumes approximately 500 uA, but is only on 10% of the time (assuming transmitting 3 bytes (24 bits) at 2400 baud once per second), resulting in 50 uA average current. A conventional CR2430 Lithium coin cell (24.5 mm diameter 3 mm thick), about the size of a quarter, has a 200 mAh capacity; enough power to run the microcontroller and transmitter for about 3.5 months. Six of these batteries can fit on a credit card (along with the electronics), producing a lifetime of approximately 1.2 years. Lifetime can be increased to three years by decreasing the reporting time to once every five seconds. Doubling the EF Card's battery count and thickness would also double the EF Card's lifetime. An on/off switch activated by the user 2 would further increase battery lifetime (assuming 8 hours on and 16 hours off, 5 days per week).

Detailed Description of Preferred Encryption Techniques

The discussion which follows gives the details of two secure implementations of the EF card described above, together with the details of the authentication server. They are summarized as follows:

1. Centralized unique ID authentication for a large population

The server uniquely identifies the cardholder, rejecting attempts at impersonation. A sample application would be a unique ID card for a population of several billion, each of whom can use the card for ATM access, driver's license, passport, phone card, credit card or other services. The crux of the system is a carefully chosen drift parameter used by the server for efficient authentication. Details of the choice of the parameter depend on the embodiment, and are given below.

2. Local authentication in autonomous locks

In the implementation given above, the assumption is that the various receivers are connected to a central authentication server. Here, instead, each receiver has a processor of its own, but is not networked to any central server. For instance, door locks in an automobile may be implemented with such stand-alone processors. A user's card can be programmed to access any subset of the locks.

The following is a detailed description of these two preferred implementations.

1. Centralized unique ID authentication

Each user has a unique ID X, represented by a bit-string, typically of length 32 bits, allowing (in this example of 32 bits) about 4 billion users to have unique bit-string IDS.

At one-second intervals, the card transmits f(X,t) (represented as a bit-string), where f( ) is an encryption function that is private to X, and t is the time (in seconds) measured from an initial synchronized starting point. A description is given below for two embodiments of the encryption function and authentication server. Also, for each, it is shown that the encryption function cannot be broken except by exhaustive (and impractical) computation.

2. Local authentication for autonomous receivers

In situations where it is not desirable to have a network connecting all the receivers (for example locks) to a central server, it is possible to use a different scheme, in which the EPROM in each EF card is programmed (at a central station) to be able to access a subset of all the receivers.

It is assumed that a processor of moderate computational power is available at each of the receivers (locks).

Figure 7:
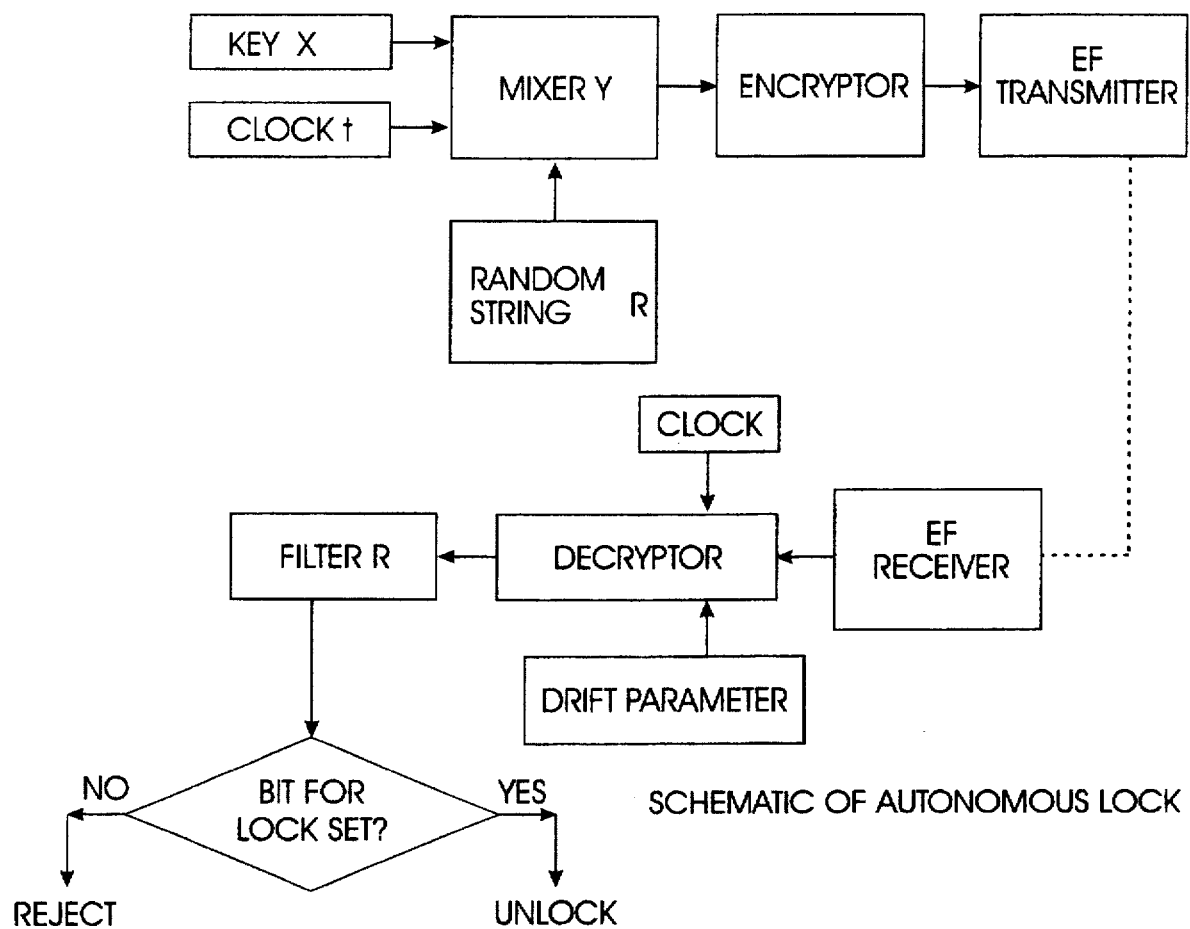

Referring to the flow chart in FIG. 7, each card is given a key X. Multiple cards may share the same key X if they are authorized access to the same receivers. The i-th bit of X denotes whether or not the i-th lock allows access to the card with key X. Thus, in a building with 500 locks, the key X would consist of 500 bits.

By interspersing X with a random-chosen string of length roughly 1000 bits, a new key Y is derived. This is used to encrypt time with a private function f(Y,t), where t as before is the time. This private function is known to all the locks, as is the random pattern by which Y is derived from X. When an attempt is made to access a lock r, the processor in the lock decrypts the transmission by inverting f and discarding the randomly interspersed bits after checking that they have the correct values, and rejects the attempt if either the bit corresponding to r is zero in X (as decrypted), or the time t does not match (within the lock drift window and, depending on the scheme, an additional window of 4 sqrt(t) seconds).

Preferably, the signal that is transmitted by the EF card (consisting of ID, time, etc) is encrypted by a public key that is known to all the cards, and can only be decrypted by a private key available to the servers. Potentially, a network of receivers according to the invention, located around a geographic area, can be used to track a person's whereabouts.

Because an apparatus according to the invention sends out what appear to be random numbers, an eavesdropper would see gibberish (random numbers) which would not reveal any information about the carrier of the card. It is only when these numbers are sent to an authenticator that they are linked with a service, such as an ATM, drivers license, calling card, etc.

In one embodiment a transmitter card is placed in the wallet, pocket, or purse of a person, and receivers are incorporated into various applications. The transmitter includes microprocessor circuitry, an electric field generator, a battery, and a time reference. The microprocessor circuitry includes identification data, control software, and encryption technology. The receiver includes an electric field receiver, a microprocessor, and a time base. The transmitter is contained in a piece of plastic about the size of a credit card, and is carried in the user's, purse, or pocket. The receiver is incorporated into an apparatus appropriate to the application.

First Embodiment of Encryption: Shift Registers

Figure 15:
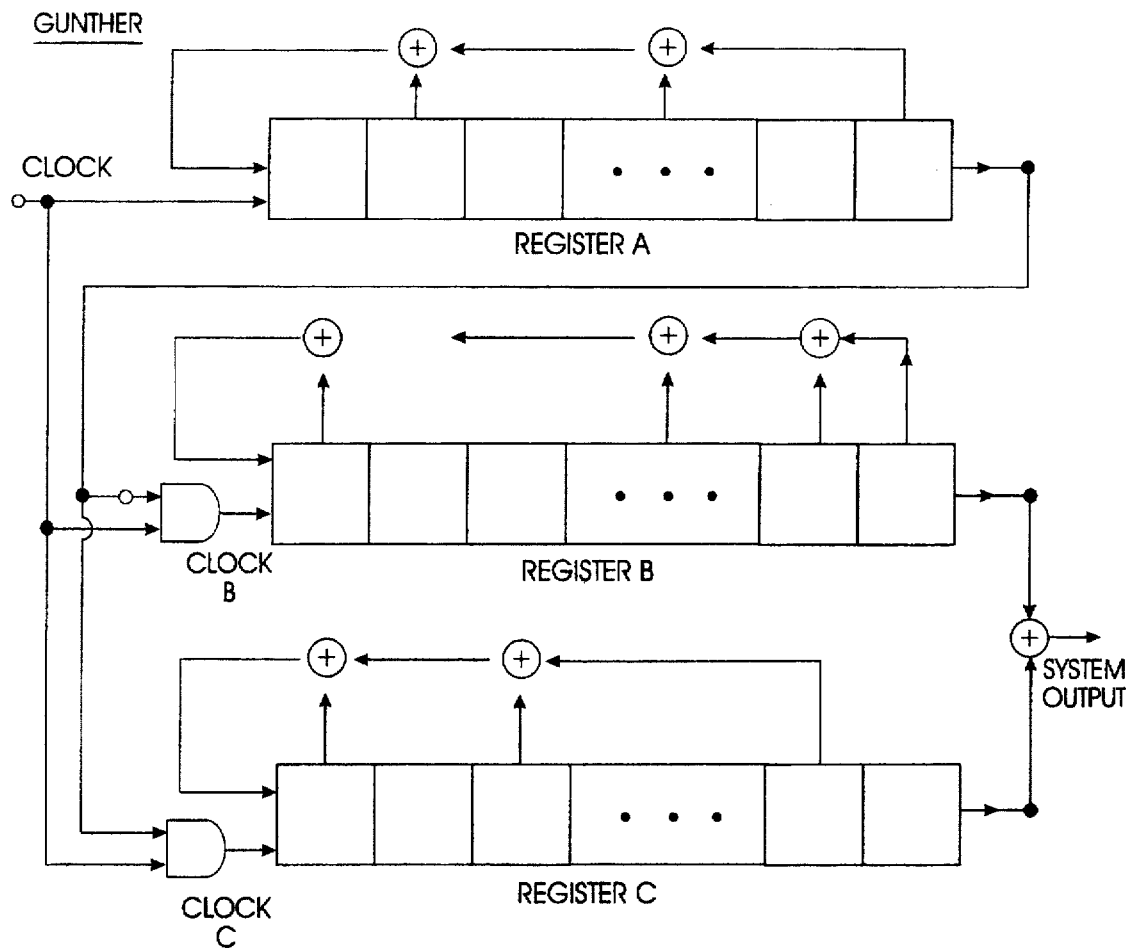
FIGS. 15 and 16 are schematic diagrams of shift register implementations of the cryptographic aspect of the invention.
Figure 16:
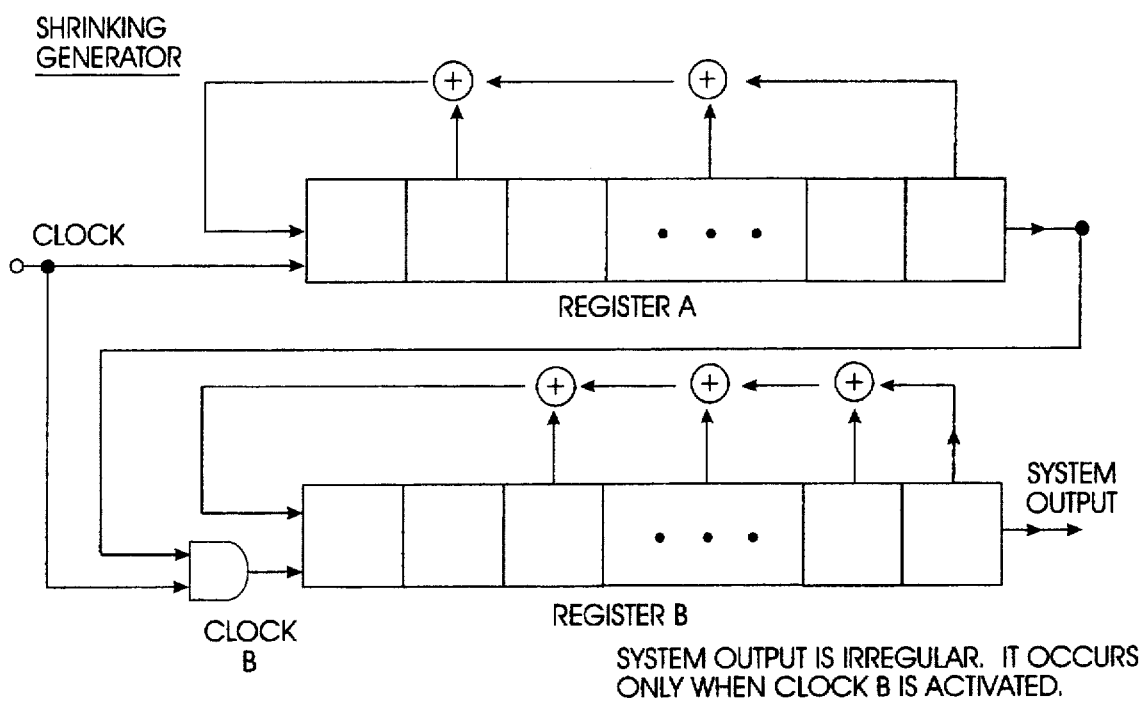

One embodiment involves shift registers. See FIGS. 15 and 16.

For additional background information on this embodiment, see the following references:
Reference(1):

C. G. Gunther, "Alternating step generators controlled by shift registers," in Lecture Notes in Computer Science 304, Advances in Cryptology: Proc. Eurocrypt '87, Berling: Springer-Verlag, 1988, pp. 88–92.

See also
Reference(2):

Don Coppersmith, Hugo Krawczyk, and Yishay Mansour, "The shrinking generator," Advances in Cryptology—CRYPTO '93, Douglas R. Stinson (Ed), Springer LNCS volume 773, 1994, pages 22–39.

D. Coppersmith, A. Herzberg, H. Krawczyk, S. Kutten, Y. Mansour, "The Shrinking Generator: a new Pseudo Random Generator for Stream Cipher Cryptosystems." Presented at ITL October 1992.

In reference (1), three shift registers, A, B, C, each of length about 100, are used. The first register A operates and outputs one bit. This bit dictates whether the second or third register B or C is used. Next, this register B or C operates and outputs one bit, which is used as the output of the system. The other register C or B is idle during this time step.

The taps (determining the polynomials) of the three registers could be common to all users, and the initial settings could be varied between users and kept as secret quantities. The user would broadcast his ID, the last 128 bits of output from his card, and his perceived time t. The server would compare the time t against the real time; recall the initial setting of the user's registers, and advance register A by t steps (which can be done quickly) and registers B and C by about t/2 steps each.

The 0-bits of output from register A would tell which of the 128 bits of system output had come from register B.

The server would examine the output of register B in the time interval between t/2−2 sqrt(t) and t/2+2 sqrt(t) to find the pattern of bits corresponding to these output bits. The exact location U depends on the number of 0-bits output by register A, and is difficult to compute quickly. The server would perform a similar computation on register C to find its location V.

If the user is legitimate, the two locations should satisfy U+V=t.

This embodiment is simple for the EF card, requiring only about 300 bits of RAM and a few hundred bits of ROM. The computational requirement for the server is somewhat more, requiring the evaluation of a string of about 4 sqrt(t), or approximately 100,000 bits of output of each register.

This novel implementation of the server's computation is substantially more efficient than brute-force checking, and enables the practical realization of a server system when (potentially) millions of EF cards are in use accessing resources concurrently.

Further, the server would typically not be exactly synchronized with every card, due to clock drift. It therefore allows authentication within a "drift window" of time of Delta seconds. That is, if t is the time according to the server, then it authenticates only if the received signal is f(X,t') for some t', where |t−t'| is at most Delta.

Reference (2) describes a similar setup but with only two shift registers. This second setup suffers from reduced security, but has a simpler implementation (only two shift registers instead of three).

It is necessary that a given signal be accepted for about sqrt(t) time steps, which should be minimized to limit the amount of time an eavesdropper has to operate.

Second Embodiment of Encryption: Data Encryption Standard (DES)

A second embodiment would involve the well-known Data Encryption Standard (DES).

Figure 6:
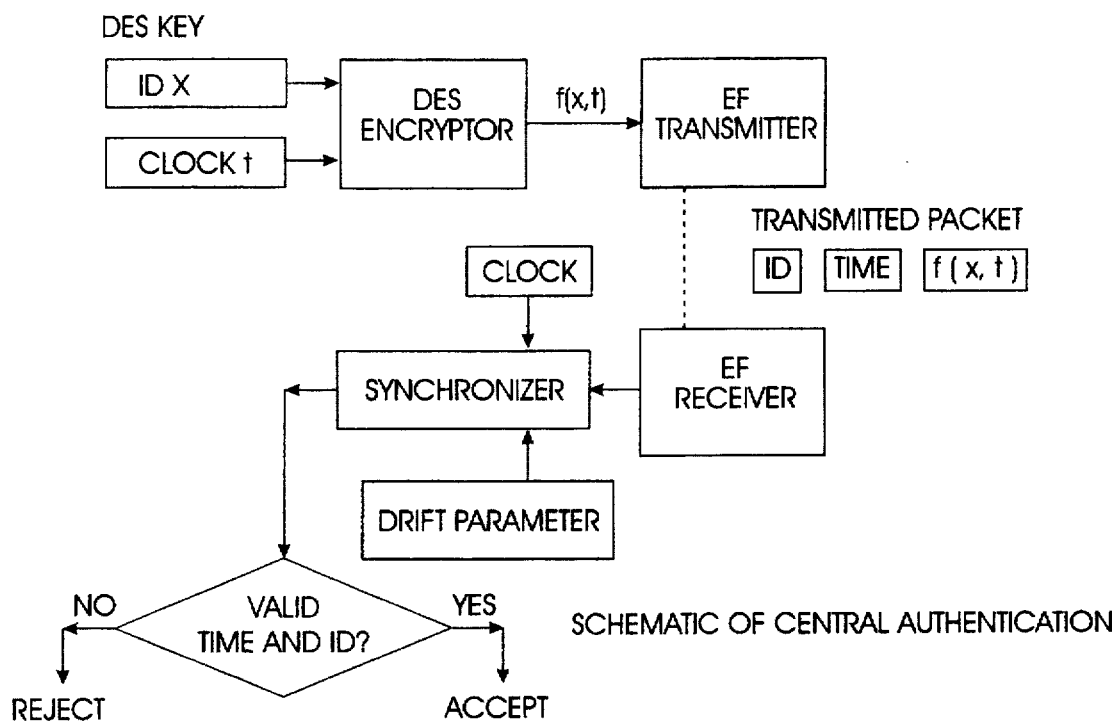
FIGS. 6 and 7 are flowcharts showing encryption procedures executed by an apparatus in accordance with the invention.

Referring to the flow chart of FIG. 6, each user would have a secret DES key X. Once every second, the card would transmit the user's ID and the DES encryption of the message t under the key X corresponding to this ID, which we can represent as f(X,t). The server would receive the ID, look up the corresponding secret key X, and check the calculation of f(X,t).

The EF card requires about 96 bits of RAM to do the DES encryption, and another 64 bits for t, and a few thousand bits of ROM for DES. (Faster implementations of DES would require some 32K bits of ROM.).

FIG. 6 also shows a typical format for a data packet as per the above description.

FIG. 14 is a pseudocode implementation of the synchronizer of FIG. 6.

Once again, the drift parameter is involved to adjust for synchronization. The drift parameter, represented as Delta, is chosen subject to the following constraints:

(1) It is large enough to swamp the sum of the clock drift and the quantity 4 sqrt(t) (for the first embodiment above).

(2) It is small enough that the "window of opportunity" for an eavesdropper cannot reuse the transmission for a substantial length of time.

The clocks at the server and the EF card cannot be expected to remain in perfect synchrony. The server therefore allows a clock synchronization window (a typical value could be 8 seconds)—an allowed differential between the card's notion of time and the server's—within which authentication would proceed. This function is implemented in the synchronizer at the server. Upon receipt of the card's signal, the server's synchronizer checks whether the card's notion of time is within 8 seconds of its own, and, if so, checks whether the card is allowed to access the server.

Each time authentication is successfully performed, the Delta time is reset to zero. There are two causes of drift, (a) the time reference of a particular card is faster or slower than the authenticator, and (b) the time reference of a particular card varies, usually due to temperature changes.

The first case is predictable, and in a preferred embodiment the authenticator calculates the frequency of each card from successive authentications. Time drifts due to temperature changes are usually minimal, since the card is typically kept with a person at room temperature. The stability of practical time references are demonstrated by the time keeping ability of inexpensive digital watches, which can maintain time to within a few minutes per year.

Scenarios in Which the Invention (Embodied in a Card Carried by the User) Can Be Used An object of the invention is to replace the multitude of plastic cards in a person's wallet with one universal electronic card. The invention can replace the function of many plastic cards, including a credit card, a dining card, telephone calling card, automated teller machine (ATM) cash card, health card, driver's license, video store card, frequent flyer (airplane) card, car and computer access card. The following are scenarios which demonstrate the usefulness of the EF Card in a variety of applications.

Credit Card

The reader electrode is located on a rug or in a panel located near a cash register. As the customer stands by the cash register, the identification information from the person's EF card is communicated to the receiver. When items are totaled, the customer can press a button, authorizing the purchase.

Dining Card

Figure 8:
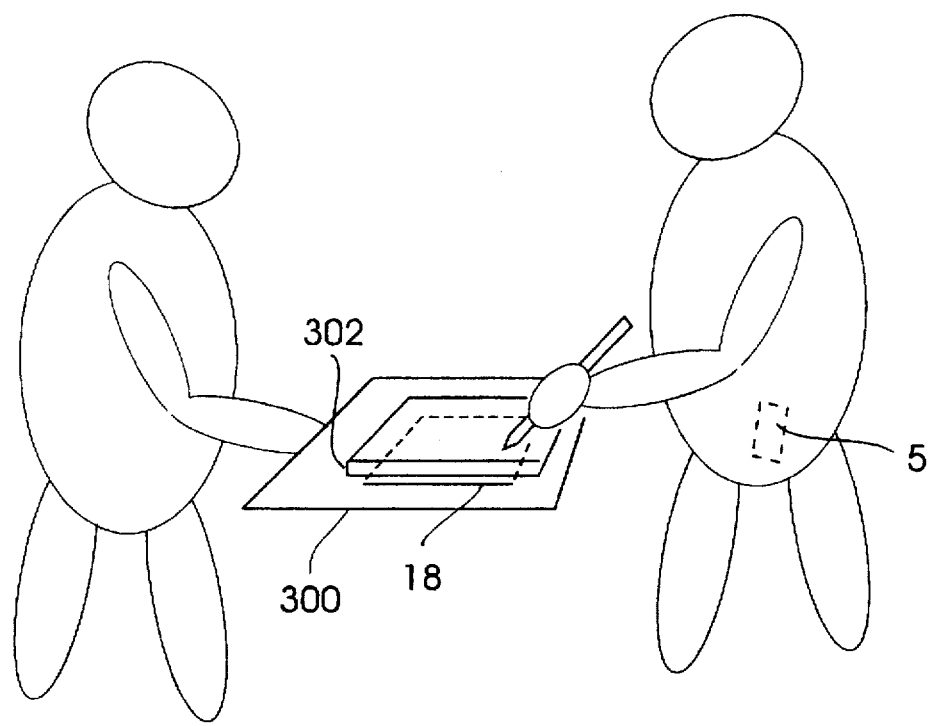
FIGS. 8, 9, 10, 11, 12, and 13 are diagrams of environments in which the invention is advantageously practiced.

Referring to FIG. 8, the reader is located in a tray 300, containing a restaurant bill 302, which the waiter brings to the customer. The customer touches the receive electrode 18 to authorize payment. If the person has several credit cards, then icons representative of the various cards are presented, and the person selects the card he/she wishes to debit. For additional security, a signature can be collected on a paper bill. By placing the receive electrode 18 below the paper bill, the electronic identification information can be collected as the customer signs.

Calling Card

Figure 9:
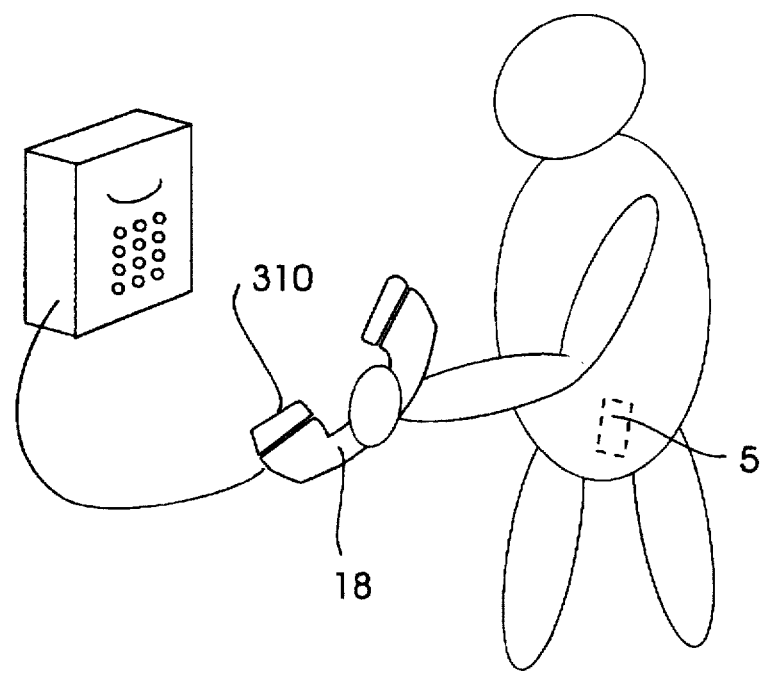

Referring to FIG. 9, the receiver electrode 18 is placed in a handset 310 of a public pay telephone. When the person picks up the handset 310, the person's identification information is uploaded from the EF card 5, through the person's hand and body and the receiver in the handset 310, to a networked computer for authorization. The upload can be occurring simultaneously to manual dialing, so that authorization can be completed without delaying or interrupting the placing of the call.

Accordingly the card 5 makes using a pay phone as convenient as using a home phone. The customer just picks up the phone and dials without fussing with a calling card or access numbers.

Health Card

Figure 10:
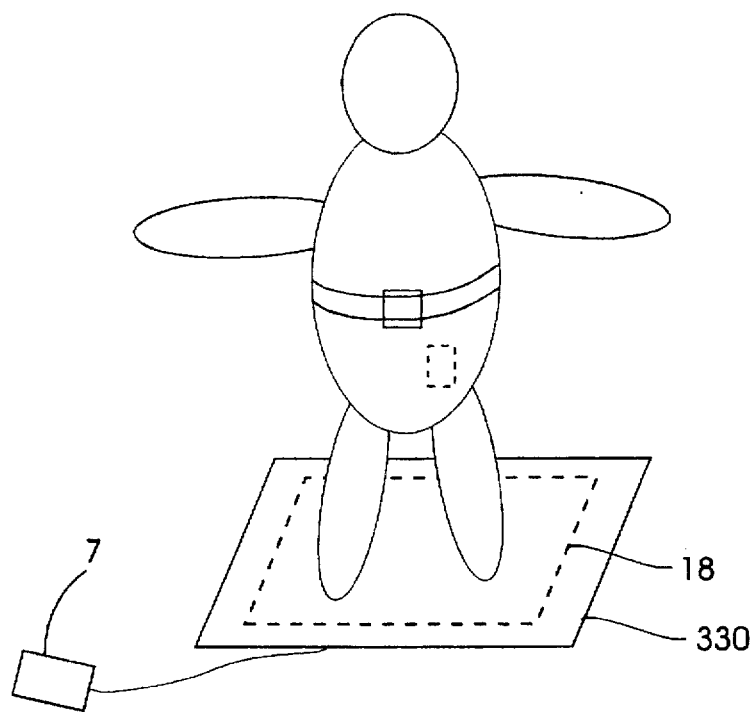

Referring to FIG. 10, the receiver electrodes 18 are located in floor mats 330 placed at all entrances to the facility, and in front of all stairs and elevators. The receiver electrodes may also be located in other fixtures or objects which a patient will likely encounter as he/she enters the facility.

When a person enters the facility, the person's identification information is detected by a receiver module 7. This information and the location of the mat are sent to the facilities computers. This information is matched with appointment information, to inform the appropriate department of the arrival of a client.

At an airport, a frequent flyer card may be used similarly, for airline reservation information.

Driver's License

A police officer carries a Personal Digital Assistant which embodies a personal area network according to the invention, and which also includes a radio link to a computer in the officer's patrol car. The receiver electrode is located inside a traffic citation log. The log includes a radio link to police headquarters. Communication, generally as discussed above, allows quick confirmation of the validity of a driver's license and access to the driver's record.

Video Store Card

Figure 11:
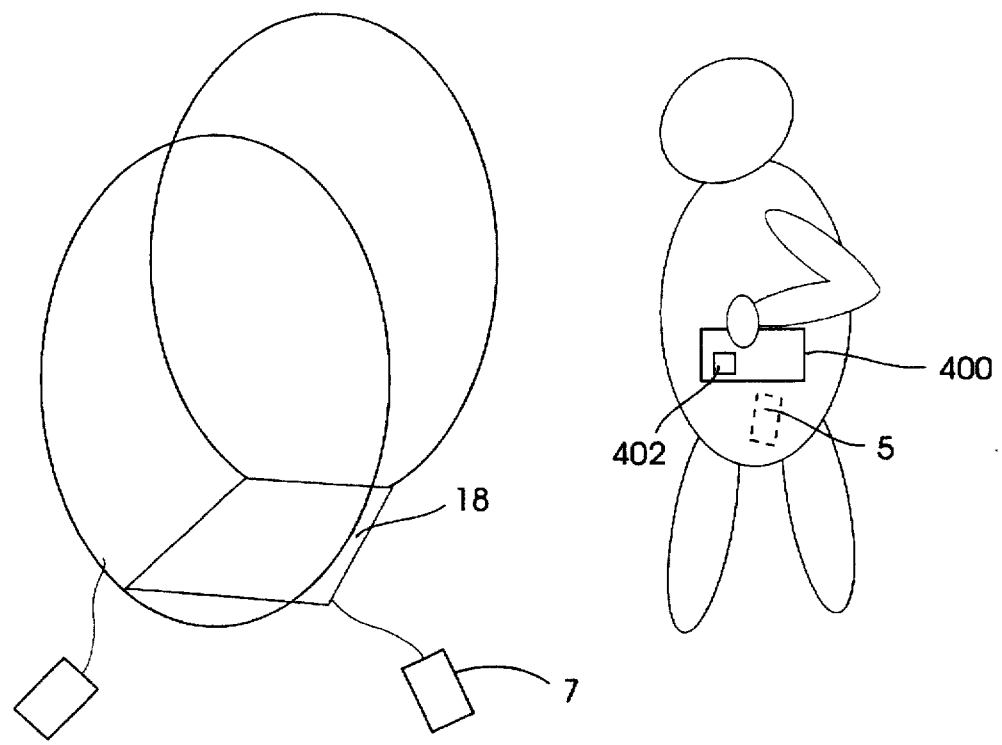

Referring to FIG. 11, the receiver electrode 18 is located in door mats near exit ways. The card 5 identification information would be used to indicate the account number of the person.

The invention can be combined with radio tag technology, which can electronically identify each video tape. A customer would select the video tapes 400 he/she wanted from the shelves, and then simply walk out of the store. Radio tags 402, mounted on each of the video tapes 400, would identify those video tapes the customer is removing, and the card 5 would identify the account to bill.

Car Access Card

Figure 12:
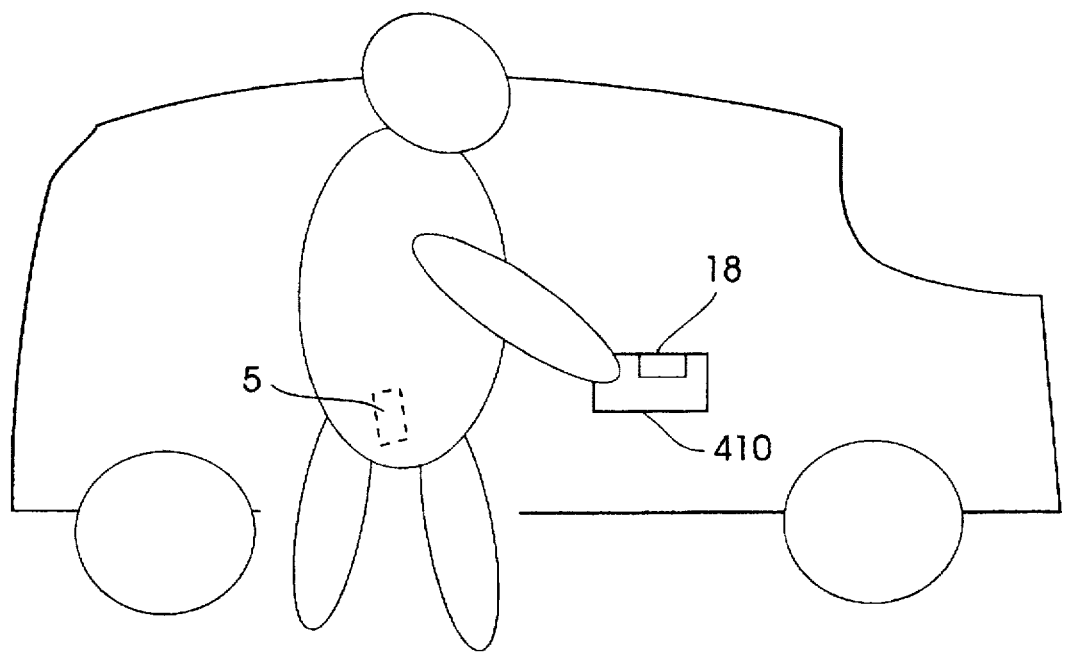

Referring to FIG. 12, the receiver electrode 18 is in a metal door handle 410. The card doors automatically unlock when the possessor of an authorized Card 5 places his/her hand on the door handle. Touching the door handle without pulling the latch within a fixed time period (e.g. 15 seconds) causes all the doors to lock.

Computer Access Card

Figure 13:
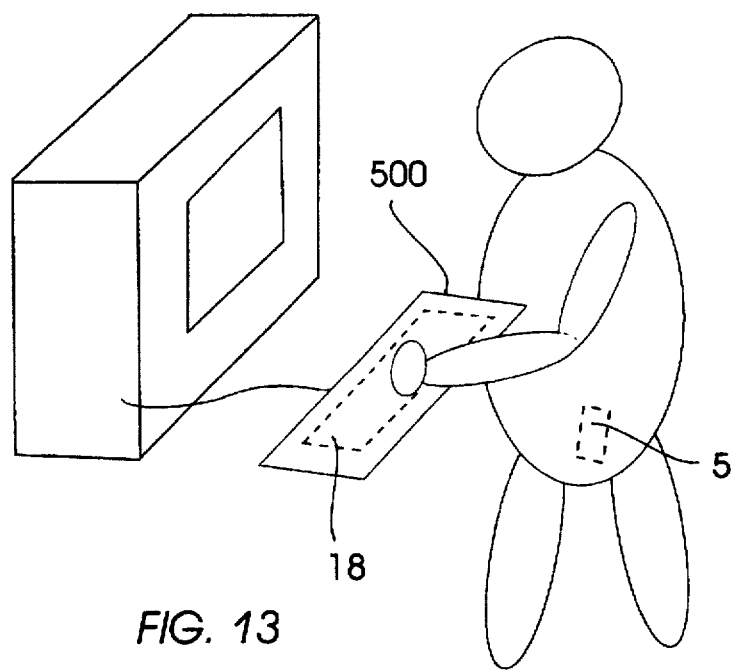

Referring to FIG. 13, the receiver electrode 18 is located underneath a computer keyboard 500. The computer keyboard is normally disabled. When the hand of a person who possesses an authorized Card 5 comes in close proximity to the keyboard, the keyboard is enabled. This arrangement prevents unauthorized people from using the computer. A similar system could be used for cash registers at restaurants and retail stores.

Statutory Classes of Embodiments

Using the foregoing specification, the invention may be implemented using standard programming and/or engineering techniques using computer programming software, firmware, hardware or any combination or subcombination thereof. Any such resulting program(s), having computer readable program code means, may be embodied or provided within one or more computer readable or usable media such as fixed (hard) drives, disk, diskettes, optical disks, magnetic tape, semiconductor memories such as read-only memory (ROM), etc., or any transmitting/receiving medium such as the Internet or other communication network or link, thereby making a computer program product, i.e., an article of manufacture, according to the invention. The article of manufacture containing the computer programming code may be made and/or used by executing the code directly from one medium, by copying the code from one medium to another medium, or by transmitting the code over a network.

An apparatus for making, using, or selling the invention may be one or more processing systems including, but not limited to, a central processing unit (CPU), memory, storage devices, communication links, communication devices, servers, I/O devices, or any subcomponents or individual parts of one or more processing systems, including software, firmware, hardware or any combination or subcombination thereof, which embody the invention as set forth in the claims.

User input may be received from the keyboard, mouse, pen, voice, touch screen, or any other means by which a human can input data to a computer, including through other programs such as application programs.

One skilled in the art of computer science will easily be able to combine the software created as described with appropriate general purpose or special purpose computer hardware to create a computer system and/or computer subcomponents embodying the invention and to create a computer system and/or computer subcomponents for carrying out the method of the invention. While the preferred embodiment of the present invention has been illustrated in detail, it should be apparent that modifications and adaptations to that embodiment may occur to one skilled in the art without departing from the spirit or scope of the present invention as set forth in the following claims.

While the preferred embodiments of the present invention have been illustrated in detail, it should be apparent that modifications and adaptations to those embodiments may occur to one skilled in the art without departing from the scope of the present invention as set forth in the following claims.

What is claimed is:

1. An electronic communication apparatus comprising:

a portable transmitter, to be carried or worn on a user's person, the transmitter including:
   (i) means for storing an item of information,
   (ii) means for producing an encrypted electrical signal representative of the item of information, and
   (iii) a physical interface for coupling the signal from the means for producing to the user's body; and a receiver including:
   (i) a physical interface for establishing an electrical coupling between the receiver and the user's body,
   (ii) means for receiving the encrypted signal from the user's body through the physical interface,
   (iii) means for decrypting the signal to obtain the item of information, and
   (iv) means for performing an action responsive to the item of information.

2. An apparatus as recited in claim 1, wherein:

the transmitter includes means for modulating; and the receiver includes means for demodulating.

3. An apparatus as recited in claim 2, wherein the means for modulating and for demodulating include direct sequence spread spectrum means for modulating and for demodulating.

4. An apparatus as recited in claim 3, wherein:

the transmitter has a unique identifier (ID);

the encrypted electrical signal has a phase; and the direct sequence spread spectrum means of the transmitter includes (i) means for synchronizing with the phase of the encrypted electrical signal, and (ii) means for delaying based on the ID of the transmitter.

5. An apparatus as recited in claim 2, wherein the means for demodulating includes On-Off keying means.

6. An apparatus as recited in claim 1, further comprising a server.

7. An apparatus as recited in claim 6, wherein the server includes the receiver.

8. An apparatus as recited in claim 6, wherein the server includes an authenticator having, for each respective user, a public ID, a private key, and a time offset value.

9. An apparatus as recited in claim 8, wherein the transmitter includes means for periodically sending authentication information.

10. An apparatus as recited in claim 9, wherein the means for periodically sending authentication information includes means for sending time-of-day information, the user's public ID, and an encrypted version of a random number.

11. An apparatus as recited in claim 6, wherein the server includes means for providing centralized unique ID authentication for a population of users, one of the users having the transmitter.

12. An apparatus as recited in claim 11, wherein:

each user has a unique ID; and the transmitter includes means for periodically transmitting a message, encrypted by an encryption function unique to the user having the transmitter, of the user's ID and a time.

13. An apparatus as recited in claim 12, wherein the means for producing an encrypted electrical signal includes:

a shift register A for outputting a bit having first and second possible states; and a shift register B which corresponds with the first possible state of the bit output from the shift register A;

a shift register C which corresponds with the second possible state of the bit output from the shift register A; and means for providing, to the physical interface, an output of the shift register B responsive to the output bit of the shift register A having the first possible state; and an output of the shift register C responsive to the output bit of the shift register A having the second possible state.

14. An apparatus as recited in claim 13, wherein:

the shift registers A, B, and C include respective sets of taps common to all users; and the apparatus further comprises means for loading initial settings into the registers, the initial settings being secret and unique to each user.

15. An apparatus as recited in claim 12, wherein the encryption function is the Data Encryption Standard (DES).

16. An apparatus as recited in claim 6, wherein the server includes means for providing local authentication for autonomous receivers.

17. An apparatus recited in claim 1, wherein the transmitter is contained within one of:

a credit card;

a dining card;

a telephone calling card;

a health card;

a driver's license;

a video store card;

a car access card; and a computer access card.

* * * * *